(12) United States Patent
Romano

(10) Patent No.: US 9,157,774 B2
(45) Date of Patent: Oct. 13, 2015

(54) DIFFERENTIAL PRESSURE FLOW SENSOR

(71) Applicant: KONINKLIJKE PHILIPS N.V., Eindhoven (NL)

(72) Inventor: Robert Romano, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/361,497

(22) PCT Filed: Dec. 12, 2012

(86) PCT No.: PCT/IB2012/057210
§ 371 (c)(1),
(2) Date: May 29, 2014

(87) PCT Pub. No.: WO2013/088351
PCT Pub. Date: Jun. 20, 2013

(65) Prior Publication Data
US 2014/0331786 A1 Nov. 13, 2014

Related U.S. Application Data

(60) Provisional application No. 61/569,486, filed on Dec. 12, 2011.

(51) Int. Cl.
*G01F 1/37* (2006.01)
*G01F 1/34* (2006.01)
*G01F 1/40* (2006.01)
*G01F 1/48* (2006.01)
(Continued)

(52) U.S. Cl.
CPC ............. *G01F 1/34* (2013.01); *A61M 16/0051* (2013.01); *G01F 1/40* (2013.01); *G01F 1/48* (2013.01); *G01N 33/497* (2013.01); *A61B 5/087* (2013.01); *A61M 2016/0027* (2013.01); *A61M 2016/0036* (2013.01); *A61M 2205/3375* (2013.01); *A61M 2205/505* (2013.01); *A61M 2205/52* (2013.01); *A61M 2205/581* (2013.01); *A61M 2205/582* (2013.01); *A61M 2205/583* (2013.01)

(58) Field of Classification Search
CPC .................................... G01F 1/37; G01F 1/22
USPC ......................................... 73/861.52, 861.53
See application file for complete search history.

(56) References Cited

U.S. PATENT DOCUMENTS 3,349,619 A 10/1967 Millar
4,118,973 A 10/1978 Tucker
(Continued)

FOREIGN PATENT DOCUMENTS

JP 20000221066 8/2000

*Primary Examiner* — Jewel V Thompson
(74) *Attorney, Agent, or Firm* — Michael W. Haas

(57) ABSTRACT

A differential pressure flow sensor that includes a plurality of channels divided into multiple sets of channels having different characteristics. Primary channels establish fluid communication between an inlet and an outlet of the flow sensor. Secondary channels establish fluid communication between the inlet and a first pressure port, but not the outlet. Tertiary channels establish fluid communication between the outlet and a second pressure port, but not the inlet. Signals generated at the first and second pressure port are used to determine a rate of flow through of gas through the sensor. Due to the structural features of the device, the phase delay of individual oscillatory flow components compared to corresponding oscillatory pressure components remains substantially constant across a wide range of flow rates.

15 Claims, 6 Drawing Sheets

(51) Int. Cl.
*A61M 16/00* (2006.01)
*G01N 33/497* (2006.01)
*A61B 5/087* (2006.01)

(56) References Cited

U.S. PATENT DOCUMENTS

| | | | |
|---|---|---|---|
| 4,403,514 A | | 9/1983 | Osborn |
| 4,961,344 A | | 10/1990 | Rodder |
| 4,993,269 A | * | 2/1991 | Guillaume et al. ........ 73/861.53 |
| 5,038,773 A | | 8/1991 | Norlein |
| 5,088,332 A | | 2/1992 | Merilainen |
| 5,313,955 A | | 5/1994 | Rodder |
| 5,347,843 A | * | 9/1994 | Orr et al. ........................ 73/1.34 |
| 5,379,650 A | | 1/1995 | Kofoed |
| 6,164,141 A | | 12/2000 | Chalvignac |
| 6,915,705 B1 | | 7/2005 | Truitt |

* cited by examiner

DIFFERENTIAL PRESSURE FLOW SENSOR

CROSS-REFERENCE TO RELATED APPLICATIONS

This patent application claims the priority benefit under 35 U.S.C. §371 of international patent application no. PCT/IB2012/057210, filed Dec. 12, 2012, which claims the priority benefit under 35 U.S.C. §119(e) of U.S. Provisional Application No. 61/569,486 filed on Dec. 12, 2011, the contents of which are herein incorporated by reference.

BACKGROUND OF THE INVENTION

1. Field of the Invention

The present disclosure pertains to systems and methods for measuring a differential pressure of a flow of gas and/or liquid in a flow body and, in particular, for measuring a differential pressure of an oscillatory flow.

2. Description of the Related Art

It is well known that some types of respiratory therapy involve the delivery of a pressurized flow of breathable gas to the airway of a subject. It is known that providing high-quality respiratory therapy, through a ventilator and/or pressure support device, hinges on accurately measuring the flow and/or (differential) pressure of a pressurized flow of breathable gas. Is it known that existing flow sensors have various restrictions and/or complications under certain operating conditions.

SUMMARY

Accordingly, it is an object of one or more embodiments of the present invention to provide a device for measuring a differential pressure of a flow of gas between an inlet and an outlet. The device includes a housing, a first and second pressure port, and a flow body. The housing forms a conduit between an inlet and an outlet. The conduit includes a first chamber and a second chamber. The first pressure port is configured to fluidly communicate with the first chamber. The second pressure port configured to fluidly communicate with the second chamber. The flow body is disposed within the conduit. The flow body includes a plurality of channels. A plurality of primary channels are disposed within the flow body. The primary channels are configured to establish fluid communication between the inlet and the outlet, such that gas from the inlet that enters the primary channels primarily flows to the outlet. A set of secondary channels is disposed within the flow body. The set of secondary channels is configured to establish fluid communication between the inlet and the first chamber such that gas from the inlet that enters the set of secondary channels primarily flows to the first pressure port through the first chamber. A set of tertiary channels is disposed within the flow body. The set of tertiary channels is configured to establish fluid communication between outlet and the second chamber such that gas that enters the set of tertiary channels primarily flows to the second pressure port through the second chamber.

It is yet another aspect of one or more embodiments of the present invention to provide a method for measuring a differential pressure of a flow of gas between an inlet and an outlet. The method includes: providing gas to a flow inlet of a flow body, wherein the flow body comprises a plurality of channels, wherein the gas includes one or more pressure perturbations, and wherein individual ones of the one or more pressure perturbations have a frequency ranging between 0 Hz and 20 Hz; establishing fluid communication for the primary channels of the plurality of channels between the flow inlet and the flow outlet, such that gas from the inlet that enters the primary channels primarily flows to the outlet; establishing fluid communication for a set of secondary channels of the plurality of channels between the flow inlet and a first chamber of a housing arranged such that the flow body is disposed within the housing, such that gas from the flow inlet that enters the set of secondary channels primarily flows into the first chamber; establishing fluid communication for a set of tertiary channels of the plurality of channels between the flow outlet and a second chamber of the housing, such that gas that enters the set of tertiary channels primarily flows into the second chamber; establishing fluid communication between the first chamber and a first pressure port of the housing, such that gas flowing into the first chamber from the flow inlet primarily flows to the first pressure port; establishing fluid communication between the second chamber and a second pressure port of the housing, such that gas flowing into the second chamber primarily flows to the second pressure port; generating first output signals conveying information related to one or more pressure and/or flow rate parameters of the gas at or near the first pressure port; generating second output signals conveying information related to one or more pressure and/or flow rate parameters of the gas at or near the second pressure port; and determining a flow based on the first output signals and the second output signals, wherein the flow includes flow perturbations, wherein individual ones of the flow perturbations correspond to individual ones of the pressure perturbations, and wherein individual ones of the flow perturbations have a phase delay compared to a corresponding pressure perturbation that remains substantially constant across flow rates of the gas ranging between minus 400 standard liter per minute (SLPM) and 400 SLPM.

It is yet another aspect of one or more embodiments to provide a system configured to measure a differential pressure of a flow of gas between an inlet and an outlet. The system includes: means for receiving gas at a flow body, wherein the flow body comprises a plurality of channels, wherein the gas includes one or more pressure perturbations, and wherein individual ones of the pressure perturbations have a frequency ranging between 0 Hz and 20 Hz; means for establishing fluid communication for primary channels of the plurality of channels between the flow inlet and the flow outlet, such that gas from the inlet that enters the primary channels primarily flows to the outlet; means for establishing fluid communication for a set of secondary channels of the plurality of channels between the flow inlet and a first chamber of a housing arranged such that the flow body is disposed within the housing, such that gas from the flow inlet that enters the set of secondary channels primarily flows into the first chamber; means for establishing fluid communication for a set of tertiary channels of the plurality of channels between the flow outlet and a second chamber of the housing, such that gas that enters the set of tertiary channels primarily flows into the second chamber; means for establishing fluid communication between the first chamber and a first pressure port of the housing, such that gas flowing into the first chamber from the flow inlet primarily flows to the first pressure port; means for establishing fluid communication between the second chamber and a second pressure port of the housing, such that gas flowing into the second chamber primarily flows to the second pressure port; means for generating first output signals conveying information related to one or more pressure and/or flow rate parameters of the gas at or near the first pressure port; means generating second output signals conveying information related to one or more pressure and/or flow rate parameters of the gas at or near the second pressure port; and means for determining a flow based on the first output signals and the second output signals, wherein the flow includes one or more flow perturbations, wherein individual ones of the flow perturbations correspond to individual ones of the pressure perturbations, and wherein individual ones of the flow perturbations have a phase delay compared to a corresponding pressure perturbation that remains substantially constant across flow rates of the gas ranging between minus 400 standard liter per minute (SLPM) and 400 SLPM.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the figures and are not limiting upon the claims unless expressly recited therein.

Figure 1:
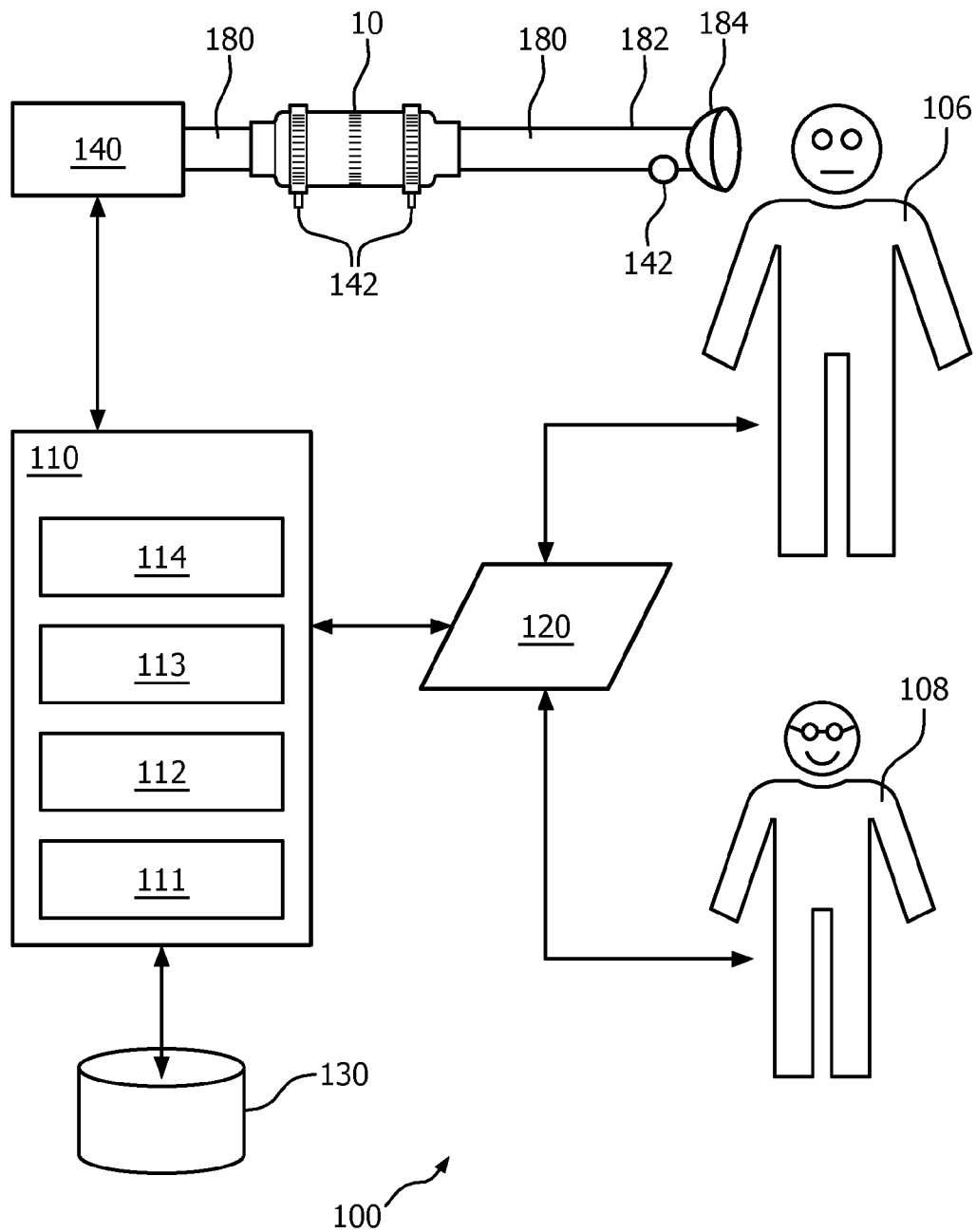
FIG. 1 schematically illustrates a pressure support system that includes a device for measuring a differential pressure of a flow of gas, in accordance with one or more embodiments.

FIG. 1 schematically illustrates a pressure support system 100 that includes a device 10 for measuring a differential pressure of a flow of gas and/or liquid, in accordance with one or more embodiments. The remainder of this description, including the examples and embodiments, will simply refer to a flow of gas, but it is contemplated that a device structurally similar to device 10 or substantially similar to device 10 may be used for measuring a differential pressure and/or impedance in a flow of liquid or a combined flow including one or more of a gas, a liquid, solid matter, an emulsion, a suspension, a colloid, and/or other combinations. It is noted that a pressure support system similar to or substantially the same as pressure support system 100 is merely an exemplary system that includes device 10.

Common devices that may perform one or more functions of device 10 in conventional systems and/or applications include differential pressure transducers, flow sensors, flow meter sensors, flow resistive elements, pressure gauges, manometers, pressure sensors, and/or other devices. However, such conventional devices are typically concerned mostly with the flow to (static) pressure relation and/or function, and, in particular, with ensuring a linear (or approximately linear) relationship between pressure and flow. As a result, conventional devices may be poorly suited for measuring a differential pressure and/or an impedance of oscillatory flows, in particular with regards to (non-constant) phase delay.

Oscillatory flows as used, described, and/or measured herein include one or more perturbations, such that individual ones of the perturbations have a frequency ranging in a predetermine range of frequencies. For example, perturbations may include pressure perturbations of the gas provided at the inlet of device 10. For example, the frequencies may range between 0 Hz and 50 Hz, between 0 Hz and 20 Hz, between 2 Hz and 10 Hz, and/or other ranges. Other frequencies for perturbations are contemplated. Multiple concurrent perturbations having different frequencies are contemplated. Device 10, as described below, is shown to have an impedance for the gas that remains substantially constant across flow rates ranging between, e.g., minus 400 standard liter per minute (SLPM) and 400 SLPM. Other flow rate ranges are contemplated. Device 10, as described below, is shown to have a phase delay for oscillatory components in the flow of gas ranging between –1 ms and 1 ms across flow rates ranging between minus 400 SLPM and 400 SLPM. Other ranges for the phase delay are contemplated. Other flow rate ranges, in relation to phase delay characteristics of various embodiments, are contemplated.

It is noted that a device such as device 10 may be used in ventilation systems and/or other systems for providing respiratory therapy besides pressure support systems (PAP/CPAP/BiPAP®/etc.). For example, in some embodiments a pressurized flow of gas may be provided by the lungs of a subject. In some embodiments, a device such as device 10 may be used in a, e.g. handheld, diagnostic system to determine, e.g., pulmonary impedance. It is contemplated that a device such as device 10 may have applications in fields outside of respiratory care and/or beyond medical applications. The scope of the presented technology is not intended to be limited by the examples, system, and/or embodiments provided in this description. Pressure support system 100 may simply be referred to herein as system 100.

System 100 in FIG. 1 is configured to provide a pressurized flow of gas for delivery to the airway of a subject 106. System 100 may be implemented as, integrated with, and/or operating in conjunction with a respiratory therapy device, such as, e.g., a ventilator.

System 100 includes a pressure generator 140, device 10, a subject interface 180, a subject interface appliance 184, a conduit 182, sensors 142, an electronic storage 130, a user interface 120, a processor 110, a parameter determination module 111, a control module 112, a timing module 113, a source of breathable gas, and/or other components. Device 10 may be included in the respiratory circuit from pressure generator, via subject interface 180 and subject interface applicant 184, to the airway of subject 106.

Figure 2A:
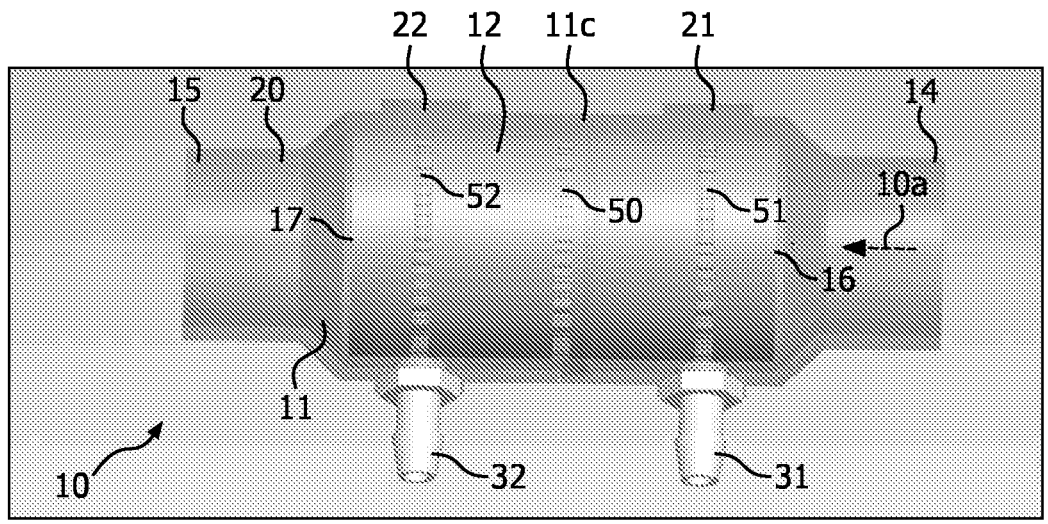
FIGS. 2A-2B illustrate perspective views of a device for measuring a differential pressure of a flow of gas between an inlet and an outlet, according to one or more embodiments.

Device 10 of system 100 in FIG. 1 is configured to provide a way to measure a differential pressure of a flow of gas, and/or a related unit that corresponds to the differential pressure across device 10 according to a known mathematical relation. By way of illustration, FIG. 2A illustrates a perspective view of device 10 for measuring a differential pressure of a flow of gas between an inlet 14 and an outlet 15 of a housing 11. Device 10 includes a housing 11, inlet 14, outlet 15, a flow body 12, and/or other components.

Housing 11 of device 10 in FIG. 2A forms a conduit 20 between inlet 14 and outlet 15. The general direction of the flow of gas is depicted in FIG. 1 as a direction 10a. Housing 11 includes a first chamber 21, a second chamber 22, a first pressure port 31, a second pressure port 32, and/or other components. First pressure port 31 is configured to fluidly communicate with first chamber 21. Second pressure port 32 is configured to fluidly communicate with second chamber 22. As depicted in FIG. 1, a pressure and/or flow rate measurement for device 10 may be made using one or more sensors 142 that fluidly communicate with first pressure port 31 and/or second pressure port 32. Referring to FIG. 2A, the constituent components and/or portions of housing 11 may be combined and/or connected by, e.g., mating element 11c. Such a combination and/or connection may be made permanent, or substantially permanent via adhesive, ultrasonic weld, bonding, snap fit, press fit, friction fit, fasteners, and/or other mechanisms for mating components.

Flow body 12 of device 10 in FIG. 2A is disposed within housing 11. Flow body 12 includes a flow inlet 16, a flow outlet 17, a plurality of channels configured to establish fluid communication between, e.g., flow inlet 16 and flow outlet 17, and/or other components. Flow inlet 16 of flow body 12 fluidly communicates with inlet 14 of housing 11 during operation of device 10. Flow outlet 17 of flow body 12 fluidly communicates with outlet 15 of housing 11 during operation of device 10. By way of illustration, FIG. 2B illustrates an exploded perspective view of device 10 for measuring a differential pressure of a flow of gas between an inlet 14 and an outlet 15 of a housing 11.

Figure 2B:
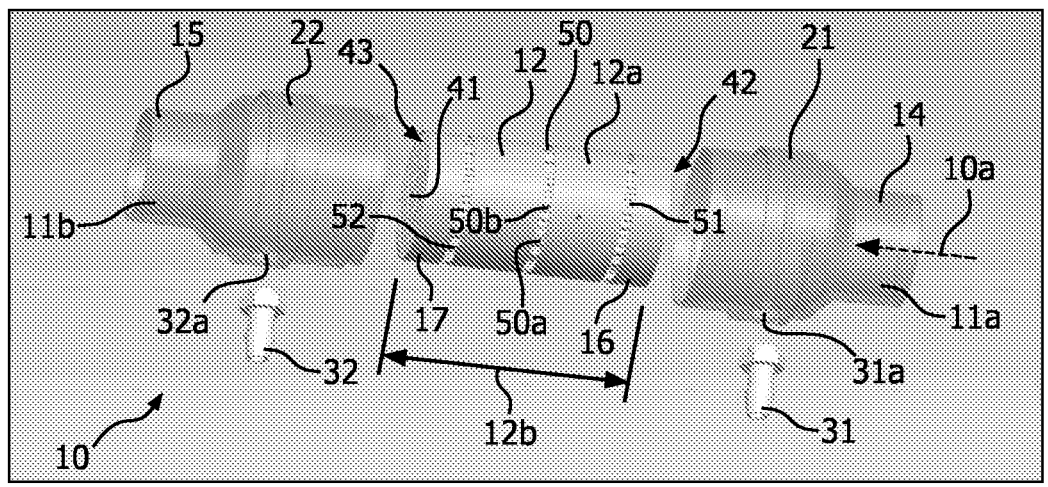

As depicted in FIG. 2B, the plurality of channels of flow body 12 include a first set of channels 41, a second set of channels 42, a third set of channels 43, a flow body surface 12a, flow directors 50, 50a, 50b, 51, 52, and/or other components. First set of channels 41 may be referred to as primary channels. Second set of channels 42 may be referred to as a set of secondary channels 42. Third set of channels 43 may be referred to as a set of tertiary channels 43. A flow director may direct and/or block a flow of gas in and/or from a particular direction or source. For example, one or more flow directors 50 may include a blocking structure that may be formed by an obstructed groove through the surface of flow body 12 such that fluid communication between opposite sides of flow director 50 is prevented. Flow directors 51 may be referred to as inlet-side flow directors 51. Flow directors 52 may be referred to as outlet-side flow directors 52. Flow directors 50 may be referred to as blocking flow directors 50. A channel of flow body 12 may interchangeably be referred to as a capillary tube.

As depicted in FIG. 2B, housing 11 includes a first housing portion 11a and a second housing portion 11b, corresponding to the sections of housing 11 that include inlet 14 and outlet 15, respectively. First engagement point 31a indicates the point of engagement between first pressure port 31 and housing 11, in particular first chamber 21. Second engagement point 32a indicates the point of engagement between second pressure port 32 and housing 11, in particular second chamber 22. The depiction of FIG. 2B is not intended to limit how device 10 can be manufactured. In some embodiments, first pressure port 31 and second pressure port 32—as well as aligned features first chamber 21, second chamber 22, flow directors 51, and flow directors 52—are recessed from flow inlet 16 and flow outlet 17, respectively, by a predetermined distance. The predetermined distance may be relative to the total length/height of flow body 12, and/or may be an absolute distance of about 0.25 inch, about 0.5 inch, about 1 inch, between about 0.5 and 0.1 inch, and/or other distances or ranges of distances.

In some embodiments, flow body 12 may include an extruded ceramic substrate composed of one or more of Cordierite, and/or other mineral compositions, Mullite, Alumina, Activated Carbon, Fused Silica, corrugated metal, and/or other suitable materials that sufficiently resist the exchange of pressure at opposite surfaces of a channel.

Figure 3A:
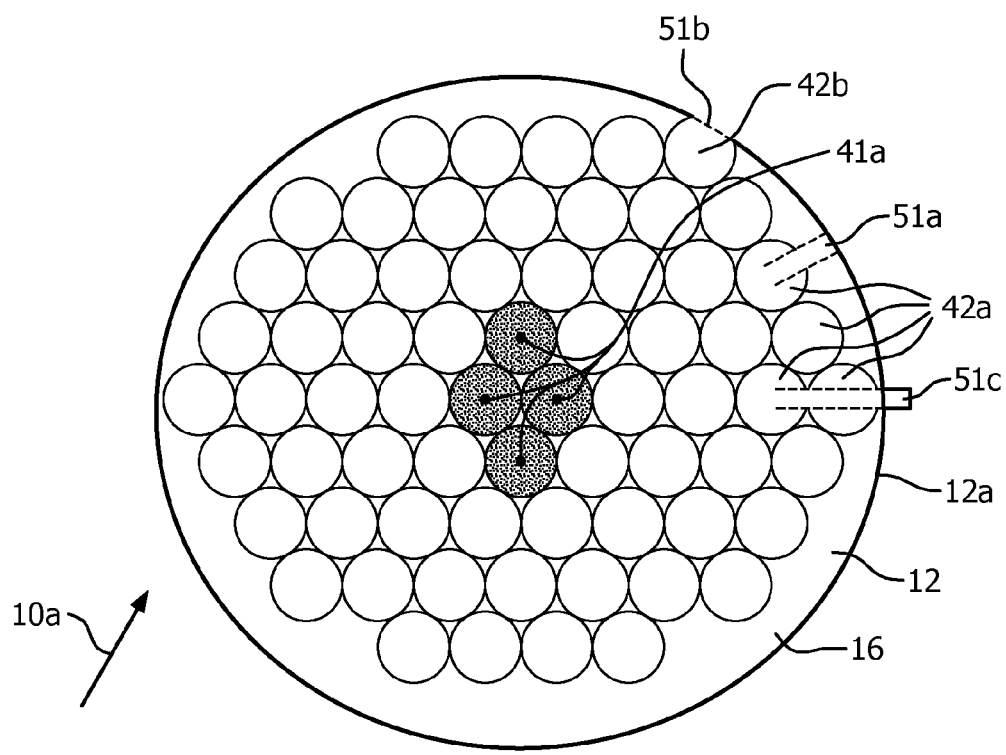
FIGS. 3A-3B illustrate views of a flow body according to one or more embodiments.
Figure 3B:
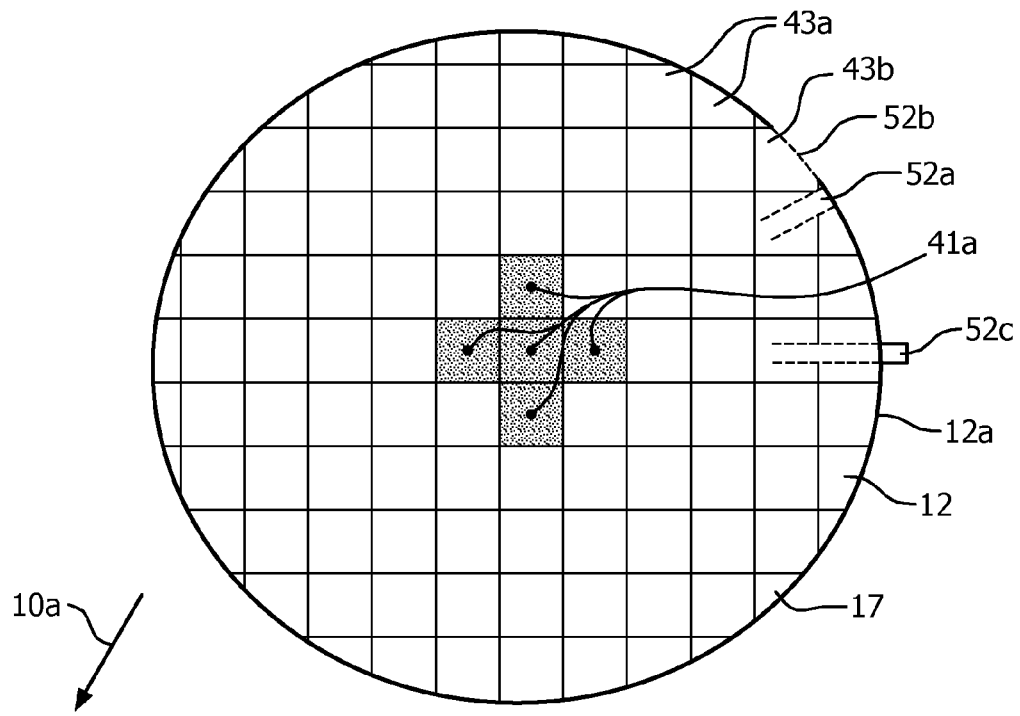

Chamber 21 and chamber 22 of housing 11 in FIGS. 3A and 3B fluidly communicate with multiple channels such that the flow inside these chambers and through the associated pressure ports may be aggregated and/or averaged. In some embodiments, chamber 21 fluidly communicates with at least 10 channels, at least 20 channels, between about 30 and 50 channels, at least 50 channels, at least 100 channels, and/or another number or range of channels of second set of channels 42. Correspondingly, one or more inlet-side flow directors 51 may include at least 10 flow directors, at least 20 flow directors, between about 30 and 50 flow directors, at least 50 flow directors, at least 100 flow directors, and/or another number or range of flow directors corresponding to the number of channels in second set of channels 42. It should be noted that in some embodiments, the number of flow directors 51 does not correspond to the number of channels in second set of channels 42. Flow directors 51 may extend annularly around flow body 12, or may extend partially around flow body 12.

In some embodiments, chamber 22 fluidly communicates with at least 10 channels, at least 20 channels, between about 30 and 50 channels, at least 50 channels, at least 100 channels, and/or another number or range of channels of third set of channels 43. Correspondingly, one or more outlet-side flow directors 52 may include at least 10 flow directors, at least 20 flow directors, between about 30 and 50 flow directors, at least 50 flow directors, at least 100 flow directors, and/or another number or range of flow directors corresponding to the number of channels in third set of channels 43. It should be noted that in some embodiments, the number of flow directors 52 does not correspond to the number of channels in third set of channels 43. Flow directors 52 may extend annularly around flow body 12, or may extend partially around flow body 12.

The number of blocking flow directors 50 of flow body 12 may correspond to the number of channels in the set of secondary channels 42, the number of channels in the set of tertiary channels 43, the number of inlet-side flow directors 51, the number of outlet-side flow directors 52, and/or may be related and/or based on another number or consideration.

Flow directors 50 may extend annularly around flow body 12, or may extend partially around flow body 12.

Primary channels 41 disposed within flow body 12 of device 10, as shown in FIG. 2B, are configured to establish fluid communication between inlet 14, via flow inlet 16 and flow outlet 17, and outlet 15 of housing 11, such that gas from inlet 14 that enters the primary channels 41 primarily flows to outlet 15. A result from guiding a flow of gas through the primary channels 41 is that a turbulent flow of gas at inlet 14 is transformed, through device 10, into a less turbulent flow of gas at outlet 15, and/or a laminar flow of gas. A shortest distance from flow inlet 16 to flow outlet 17 of flow body may be referred to as the length of flow body 12, indicated by a length 12b in FIG. 2B. Individual channels in the primary channels 41 typically substantially extend the entire length 12b of flow body 12. In some embodiments, length 12b of flow body equals about 1 inch, about 1.5 inch, about 2 inches, about 2.5 inches, about 3 inches, about less than 3 inches, about more than ½ inch, ranging between 1 and 2 inches, and/or another distance.

Second set of channels 42 disposed within flow body 12 of device 10, as shown in FIG. 2B, is configured to establish fluid communication between inlet 14, via flow inlet 16, and first chamber 21, through flow directors 51. Flow directors 51 may be arranged in and/or through flow body surface 12a. Second set of channels 42 are configured such that gas from inlet 14 that enters second set of channels 42 primarily flows into first chamber 21 and to first pressure port 31, where it may be sensed, sampled, and/or measured by sensors 142 (not shown in FIG. 2B).

In some embodiments, flow directors 51 may be an opening, a cut, a puncture, a hole, a groove, and/or other means to fluidly communicate one or more channels to flow body surface 12a at or near a fraction of length 12b that corresponds to a location of first chamber 21 when flow body 12 is positioned within housing 11, e.g. through flow body surface 12a. Individual ones of flow directors 51 may correspond to one or more channels in second set of channels 42. Individual channels in second set of channels 42 may correspond to flow directors 51. For example, flow directors 51 may be formed by a groove through flow body surface 12a such that channels within flow body 12 fluidly communicate with first chamber 21 when flow body 12 is positioned within housing 11. Note that this example is not intended to limit how device 10 can be manufactured.

Downstream from flow directors 51, relative to direction 10a, one or more obstructions may prevent fluid communication between individual channels in second set of channels 42 and outlet 15. For example, an obstruction may be one or more blocking flow directors 50, such as, e.g., blocking flow director 50a. In some embodiments, flow directors 50 may be an opening, a cut, a puncture, a hole, a groove, and/or other means to fluidly communicate one or more channels to flow body surface 12a at or near a fraction of length 12b that corresponds to a location downstream from first chamber 21 when flow body 12 is positioned within housing 11. For example, flow directors 50 may be formed by a groove through flow body surface 12a that is filled with air-tight material, such as, e.g. glue, and/or other suitable materials. Flow directors 50 are configured and/or arranged such that one or more channels from the set of secondary channels 42 substantially do not fluidly communicate with outlet 15, which may be defined as less than 1 SLPM or 1% across a range of flow rates between −400 SLPM and 400 SLPM. In some embodiments, flow directors 50 include an O-ring. Note that this example is not intended to limit how device 10 can be manufactured. Individual ones of flow directors 50 may correspond to one or more channels in second set of channels 42. Individual channels in second set of channels 42 may correspond to flow directors 50.

Third set of channels 43 disposed within flow body 12 of device 10, as shown in FIG. 2B, is configured to establish fluid communication between outlet 15, via flow outlet 17, and second chamber 22, through flow directors 52. Flow directors 52 may be arranged in and/or through flow body surface 12a. Third set of channels 43 are configured such that gas that enters the set of tertiary channels 43 primarily flows into second chamber 22 and to second pressure port 32, where it may be sensed, sampled, and/or measured by sensors 142 (not shown in FIG. 2B).

In some embodiments, flow directors 52 may be an opening, a cut, a puncture, a hole, a groove, and/or other means to fluidly communicate one or more channels to flow body surface 12a at or near a fraction of length 12b that corresponds to a location of second chamber 22 when flow body 12 is positioned within housing 11, e.g. through flow body surface 12a. Individual ones of flow directors 52 may correspond to one or more channels in third set of channels 43. Individual channels in third set of channels 43 may correspond to one or more flow directors 52. For example, flow directors 52 may be formed by a groove through flow body surface 12a such that channels within flow body 12 fluidly communicate with second chamber 22 when flow body 12 is positioned within housing 11. Note that this example is not intended to limit how device 10 can be manufactured.

Upstream from flow directors 52, relative to direction 10a, one or more obstructions may prevent fluid communication between individual channels in third set of channels 43 and inlet 14. For example, an obstruction may be one or more blocking flow directors 50, such as, e.g., blocking flow director 50b. In some embodiments, flow directors 50 may be an opening, a cut, a puncture, a hole, a groove, and/or other means to fluidly communicate one or more channels to flow body surface 12a at or near a fraction of length 12b that corresponds to a location upstream from second chamber 22 when flow body 12 is positioned within housing 11. For example, flow directors 50 may be formed by a groove through flow body surface 12a that is filled with air-tight material, such as, e.g. glue, and/or other suitable materials. Flow directors 50 are configured and/or arranged such that one or more channels from third set of channels 43 substantially do not fluidly communicate with inlet 14. Note that this example is not intended to limit how device 10 can be manufactured. Individual ones of flow directors 50 may correspond to one or more channels in third set of channels 43. Individual channels in third set of channels 43 may correspond to flow directors 50.

In some embodiments, an individual channel from the primary channels 41 may be transformed into two channels, one of which belongs to the set of secondary channels 42, and one of which belongs to the set of tertiary channels 43. For example, an individual flow director 51, an individual flow director 52, and an individual flow director 50 may all be formed to establish fluid communication with one and the same individual channel from the primary channels 41. By subsequently preventing fluid communication through the individual blocking flow director 50, the individual channel is transformed into two spatially aligned channels, relative to the direction 10a, one of which belongs to the set of secondary channels 42, and one of which belongs to the set of tertiary channels 43. Note that this example is not intended to limit how device 10 can be manufactured.

By way of illustration, FIG. 3A illustrates a view of flow inlet 16 of flow body 12. Direction 10a is perpendicular to the plane of the page, going into the page. Some channels, such as individual channels 41a of the primary channels 41, are depicted as circular, but the shape of the channels is not meant to be limited by any of the figures. Individual channels 42a of the set of secondary channels 42 are depicted as being near and/or adjacent to flow body surface 12a. In some embodiments, near and/or adjacent to flow body surface 12a, partial channels may be formed in flow body 12, such as, e.g., channel 42b of the set of secondary channels 42. A inlet-side flow director 51b may be formed, as depicted in FIG. 3A, through flow body surface 12a adjacent to individual channel 42b, such that channel 42b fluidly communicates through flow director 51b.

In some embodiments, a flow director such as flow director 51a may be formed in flow body 12, e.g. by drilling a hole through flow body surface 12a. In some embodiments, a flow director such as flow director 51c may be formed in flow body 12, e.g. by inserting a tubular element through flow body surface 12a. Note that flow directors such as, e.g., flow directors 51a, 51b, and/or 51c, may be formed through multiple layers of channels. Note that this figure is not intended to limit how device 10 can be manufactured. The number of channels depicted in FIG. 3A is not intended to be limiting. A typical density of channels may range from about 200 channels per square inch (cpsi), to about 300 cpsi, about 400 cpsi, about 500 cpsi, about 600 cpsi, between about 200 cpsi and 400 cpsi, between about 300 cpsi and 600 cpsi, between about 500 cpsi and 1000 cpsi, at least about 600 cpsi, and/or other densities.

In some embodiments, the density of channels within the flow body may not be uniform. For example, a cross-section the flow body of such an embodiment may include a single primary channel in the center (not shown in FIG. 3A-3B), surrounded by multiple secondary and/or tertiary channels adjacent to and/or near the surface of such a flow body. It is noted that such an embodiment does not transform the flow of gas from turbulent to less turbulent (or substantially laminar) to the same degree as an embodiment with a typical and/or uniform density of channels within the flow body.

FIG. 3B illustrates a view of flow outlet 17 of flow body 12. Direction 10a is perpendicular to the plane of the page, coming out of the page. The one or more embodiments depicted by FIG. 3B are not implied to be the same embodiments are those depicted in FIG. 3A. Referring to FIG. 3B, some channels, such as individual channels 41a of the primary channels 41, are depicted as rectangular, but the shape of the channels is not meant to be limited by any of the figures. Individual channels 43a of the set of tertiary channels 43 are depicted as being near and/or adjacent to flow body surface 12a. In some embodiments, near and/or adjacent to flow body surface 12a, partial channels may be formed in flow body 12, such as, e.g., individual channel 43b of the set of tertiary channels 43. An outlet-side flow director 52b may be formed, as depicted in FIG. 3B, through flow body surface 12a adjacent to channel 43b, such that channel 43b fluidly communicates through flow director 52b. In some embodiments, a flow director such as flow director 52a may be formed in flow body 12, e.g. by drilling a hole through flow body surface 12a. In some embodiments, a flow director such as flow director 52c may be formed in flow body 12, e.g. by inserting a tubular element through flow body surface 12a. Note that flow directors, such as flow directors 52a, 52b, and/or 52c, may be formed through multiple layers of channels. Note that this figure is not intended to limit how device 10 can be manufactured.

Figure 4:
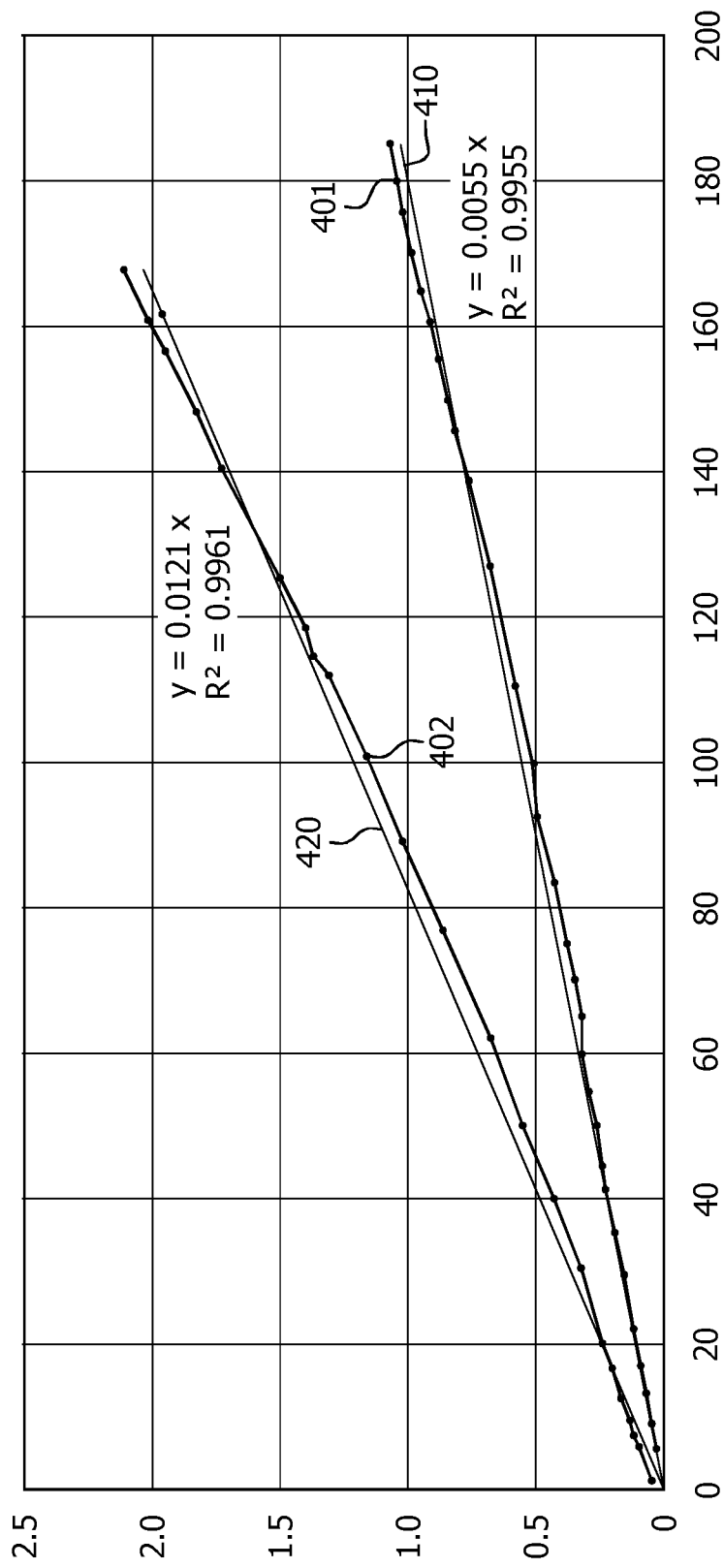
FIG. 4 illustrates a diagram pertaining to the pressure drop across a flow body according to one or more embodiments.

FIG. 4 illustrates a diagram 400 pertaining to the pressure drop measured across flow body 12 according to one or more embodiments. The Y-axis indicates pressure drop, in cmH$_2$O. The X-axis indicates flow rate, in L/min. Relation 401 illustrates a pressure drop, for one or more particular embodiments, that is substantially linear (cf. function 410) in, at least, a range of (human) physiologically relevant flow rates, such as 0-190 L/min. The laminar flow represented by relation 401 can be calculated to have a Reynolds number R such that $R^2$ equals 0.9955. Relation 402 illustrates a pressure drop, for a particular embodiment, that is substantially linear in the same range (cf. function 420). The laminar flow represented by relation 402 can be calculated to have a Reynolds number such that $R^2$ equals 0.9961. For practical purposes, embodiments of flow body may be configured such that the corresponding Reynolds number is such that $R^2$ is at least about 0.97, at least about 0.98, at least about 0.99, at least about 0.995, and/or at least about another threshold indicating how close the flow of gas resembles an ideal laminar flow. In other words, a turbulent flow of gas at the inlet of flow body 12 is transformed into a less turbulent flow at the outlet of flow body 12.

Figure 5:
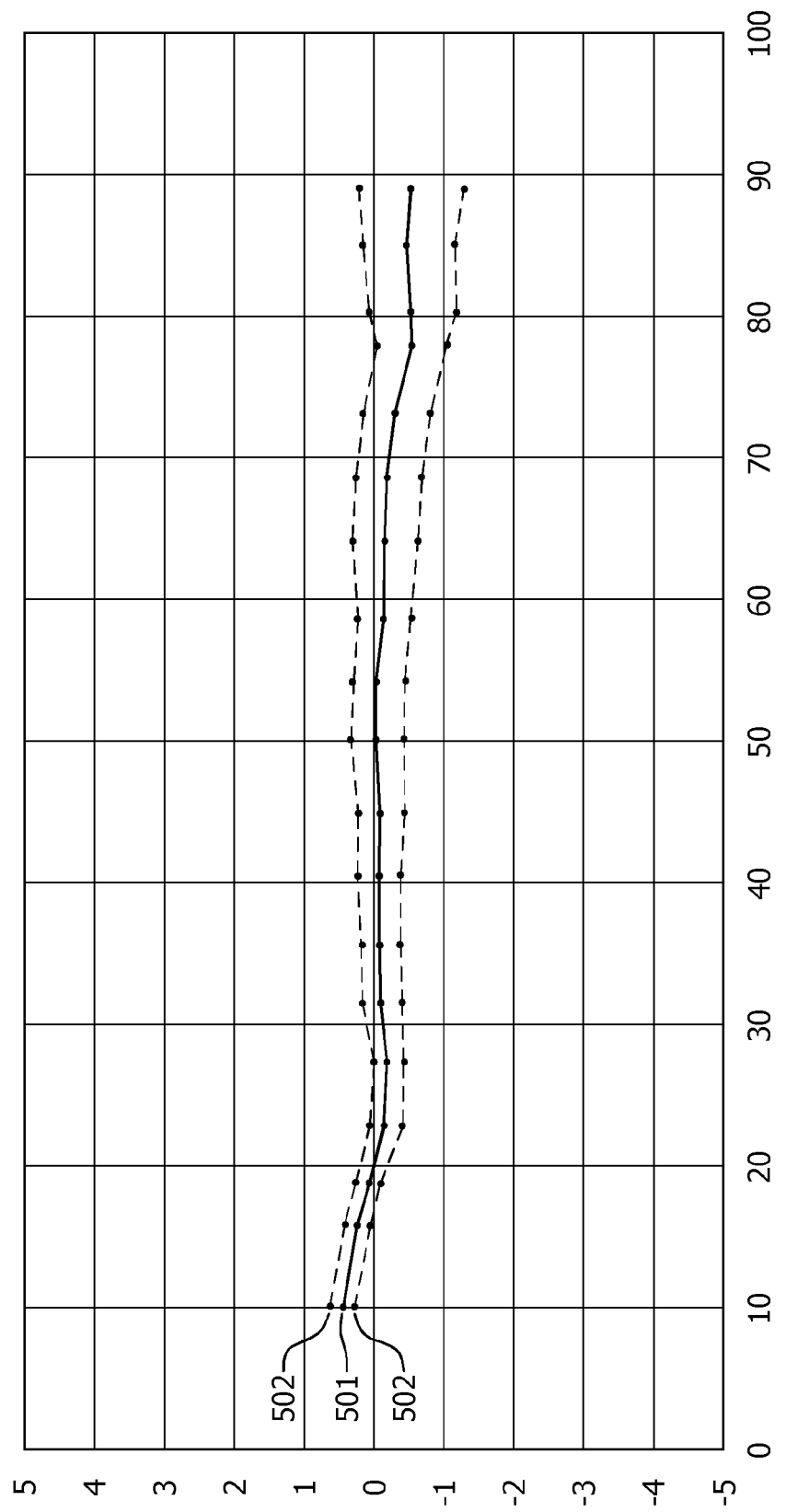
FIG. 5 illustrates a diagram pertaining to the phase delay across a flow body according to one or more embodiments.

FIG. 5 illustrates a diagram 500 pertaining to the phase delay across flow body 12, as based on measurements taken at the pressure ports and compared to the gas provided at, e.g., inlet 14, according to one or more embodiments. The Y-axis indicates phase delay, in ms. The X-axis indicates flow rate, in L/min. Relation 501 illustrates a phase delay, for one or more particular embodiments, that is between about minus 1 ms and 1 ms across a range of flow rates. The range of flow rates depicted in FIG. 5 ranges approximately between 10 SLPM and 90 SLPM. In some embodiments, other ranges for the phase delay, such as between minus 0.5 ms and 0.5 ms, or between minus 2 ms and 2 ms, are contemplated. Other ranges for the flow rates, such as between −100 SLMP and 100 SLPM, or between −250 SLPM and 250 SLPM, or between −400 SLPM and 400 SLPM are contemplated. Relation 502 illustrates noise pertaining to relation 501. As the flow rate increases, the amount of noise in the measurements of phase delay may increase gradually.

Flow body 12 exhibits, thanks in part to having very low phase delay across a wide range of flow rates, a substantially constant impedance. In some embodiments, a flow body similar to flow body 12 exhibits a substantially constant phase delay. A substantially constant phase delay may be defined as ranging within a predetermined range of phase delay, as determined by the difference between the largest and smallest phase delay within a given set of operating conditions. For example, a phase delay ranging from 8 ms to 9 ms across a particular range of flow rates may be considered substantially constant. The predetermined range of phase delay that may be considered substantially constant may be 0.5 ms, 1 ms, 2 ms, and/or other size of the range of phase delay. As depicted in FIG. 5, a phase delay ranging between −1 ms and 1 ms may be considered not only substantially constant, but even substantially zero.

Referring to FIG. 1, pressure generator 140 of system 100 may be integrated, combined, or connected with a ventilator and/or (positive) airway pressure device (PAP/CPAP/Bi-PAP®/etc.) and configured to provide a pressurized flow of breathable gas for delivery to the airway of subject 106, e.g. via subject interface 180. Subject 106 may or may not initiate one or more phases of respiration. Ventilation therapy may be implemented as pressure control, pressure support, and/or volume control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Other schemes for providing respiratory support through the delivery of the pressurized flow of breathable gas are contemplated. Pressure generator 140 may be configured to adjust pressure levels, flow, humidity, velocity, acceleration, and/or other parameters of the pressurized flow of breathable gas in substantial synchronization with the breathing cycle of the subject. Sources of breathable gas, such as air from the ambient atmosphere or a tank, oxygen from a tank or oxygen concentrator, a mixture of gases, with or without nebulized medication or the like, are known in the art.

A pressurized flow of gas may be delivered from pressure generator 140 to the airway of subject 106 via a subject interface 180. Subject interface 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 of system 100 in FIG. 1 is configured to deliver the pressurized flow of breathable gas to the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more gas and/or respiratory parameters (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing the changes in one or more determined respiratory parameters of subject 106 throughout a period during which the subject is receiving therapy. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensors 142 of system 100 in FIG. 1 are configured to generate output signals conveying measurements related to parameters of respiratory airflow and/or airway mechanics. These parameters may include one or more of flow rate, (airway) pressure, humidity, velocity, acceleration, and/or other parameters. For example, sensor 142 may generate one or more output signals conveying information related to one or more pressure and/or flow rate parameters of the gas at or near first pressure port 31 and/or second pressure port 32. Sensor 142 may be in fluid communication with conduit 182 and/or subject interface appliance 184. Sensor 142 may generate output signals related to physiological parameters pertaining to subject 106.

The illustration of sensor 142 including two members in FIG. 1 is not intended to be limiting. System 100 may have 1 sensor 142, or more than two sensors 142. The illustration of a sensor 142 at or near subject interface appliance 184 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from sensor 142 may be transmitted to processor 110, user interface 120, electronic storage 130, and/or other components of system 100. This transmission may be wired and/or wireless.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of parameter determination module 111, control module 112, timing module 113 and/or other modules. Processor 110 may be configured to execute modules 111, 112, and/or 113 by software; hardware; firmware; some combination of software, hardware, and/or firmware; and/or other mechanisms for configuring processing capabilities on processor 110.

It should be appreciated that although modules 111, 112, and 113 are illustrated in FIG. 1 as being co-located within a single processing unit, in implementations in which processor 110 includes multiple processing units, one or more of modules 111, 112, and/or 113 may be located remotely from the other modules. The description of the functionality provided by the different modules 111, 112, and/or 113 described below is for illustrative purposes, and is not intended to be limiting, as any of modules 111, 112, and/or 113 may provide more or less functionality than is described. For example, one or more of modules 111, 112, and/or 113 may be eliminated, and some or all of its functionality may be provided by other ones of modules 111, 112, and/or 113. Note that processor 110 may be configured to execute one or more additional modules that may perform some or all of the functionality attributed below to one of modules 111, 112, and/or 113.

Parameter determination module 111 of system 100 in FIG. 1 is configured to determine one or more gas parameters, breathing parameters, and/or other parameters from output signals generated by sensor(s) 142. The one or more gas parameter may include and/or be related to one or more of (peak) flow, flow rate, (tidal) volume, (differential) pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more breathing parameters may be derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters. Parameter determination module 111 may be configured to determine, derive, measure, and/or obtain one or more parameters based on previously determined gas parameters, breathing parameters, and/or other parameters. For example, a differential pressure within system 100 may be used to determine impedance and/or phase delay for a particular (oscillatory component of the) flow of gas. Some or all of the stated functionality of parameter determination module 111 may be incorporated, shared, and/or integrated into other computer program modules of processor 110.

Control module 112 is configured to control operation of system 100 in one or more modes of operation. Control module 112 may be configured to control transitions between different therapy modes. Control module 112 may be configured to determine what the current therapy mode is, and/or share such information with other components of system 100. Control module 112 may be configured to control pressure generator 140 such that one or more gas parameters of the pressurized flow of breathable gas are varied over time in accordance with a respiratory therapy regimen. Control module 112 may be configured to control pressure generator 140 to provide the pressurized flow of breathable gas at inhalation pressure levels during inhalation phases, and at exhalation pressure levels during exhalation phases. Parameters determined by parameter determination module 111, timing module 113, and/or received through sensors 142 may be used by control module 112, e.g. in a feedback manner, to adjust one or more therapy modes/settings/operations of system 100. Alternatively, and/or simultaneously, signals and/or information received through user interface 120 may be used by control module 112, e.g. in a feedback manner, to adjust one or more therapy modes/settings/operations of system 100. Control module 112 may be configured to time its operations relative to the transitional moments in the breathing cycle of a subject, over multiple breath cycles, and/or in any other relation to any detected occurrences or determinations by timing module 113.

Timing module 113 is configured to determine whether a current respiratory phase is an inhalation phase or an exhalation phase. In some embodiments, timing module 113 may be configured to determine respiratory timing parameters and/or other timing parameters related to the operation of system 100, such as transitions in breathing between inhalations and exhalations. Respiratory timing parameters may include transitional moments that separate inhalation phases from exhalation phases and/or vice versa, breathing period, respiratory rate, inhalation time or period, exhalation time or period, start and/or end of inhalation phases, start and/or end of exhalation phases, and/or other respiratory timing parameters. One or more determinations by timing module 113 may be used, shared, and/or incorporated in other components of system 100.

Figure 6:
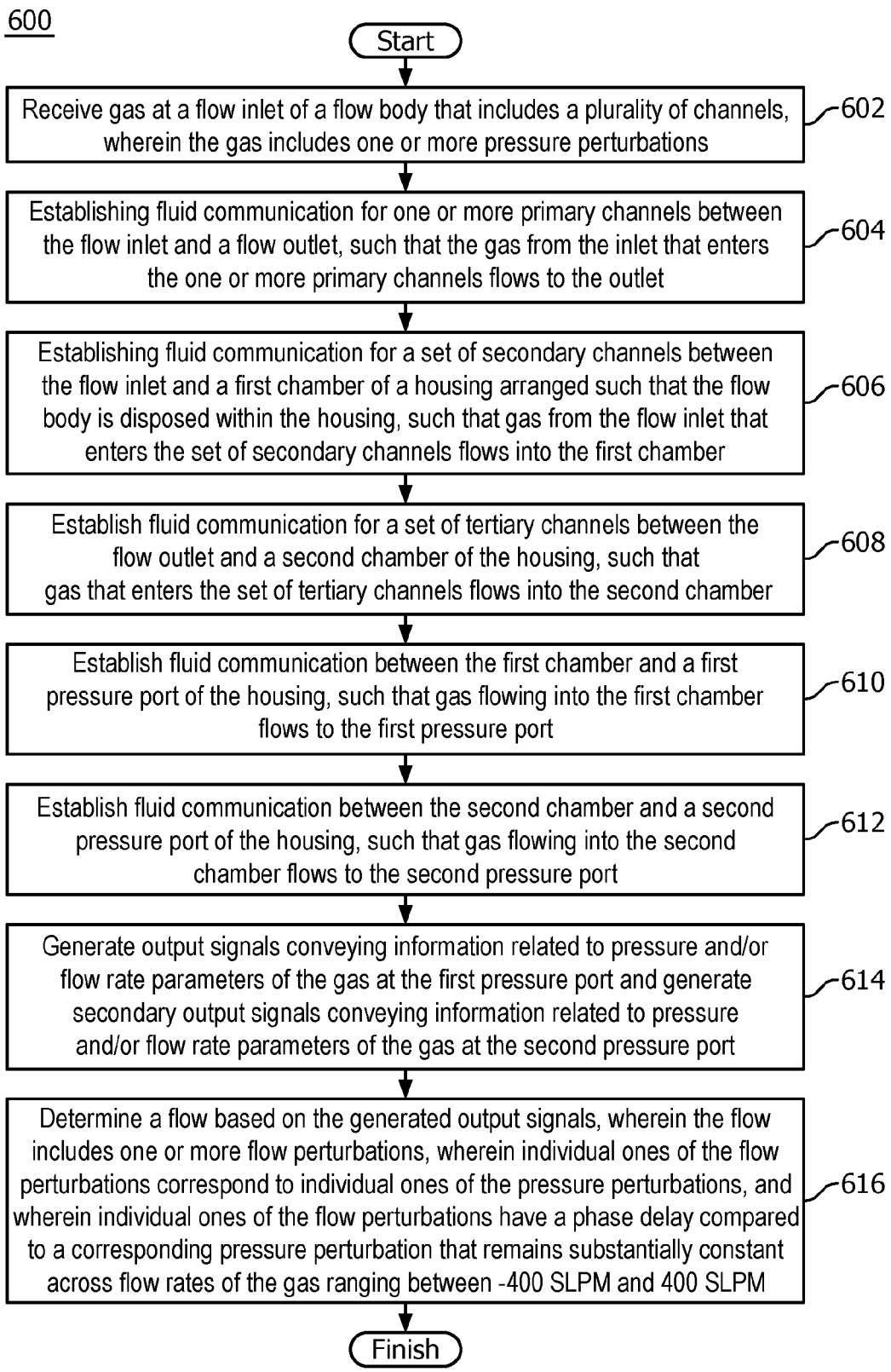
FIG. 6 illustrates a method for measuring a differential pressure of a flow of gas, according to certain embodiments.

FIG. 6 illustrates a method for measuring a differential pressure of a flow of gas between an inlet and an outlet. The operations of method 600 presented below are intended to be illustrative. In certain embodiments, method 600 may be accomplished with one or more additional operations not described, and/or without one or more of the operations discussed. Additionally, the order in which the operations of method 600 are illustrated in FIG. 6 and described below is not intended to be limiting.

In certain embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, gas is received at a flow inlet of a flow body that includes a plurality of channels, wherein the gas includes one or more pressure perturbations. In some embodiments, individual ones of these pressure perturbations have a frequency ranging between 0 Hz and 20 Hz. In one embodiment, operation 602 is performed by a flow inlet similar to or substantially the same as flow inlet 16 (shown in FIG. 2 and described above).

At an operation 604, fluid communication is established for the primary channels of the plurality of channels between the flow inlet and a flow outlet of the flow body, such that gas from the inlet that enters the primary channels primarily flows to the outlet. In one embodiment, operation 604 is performed by a set of channels similar to or substantially the primary channels 41 (shown in FIG. 2 and described above).

At an operation 606, fluid communication is established for a set of secondary channels of the plurality of channels between the flow inlet and a first chamber of a housing arranged such that the flow body is disposed within the housing. Gas from the flow inlet that enters the set of secondary channels primarily flows into the first chamber. In one embodiment, operation 606 is performed by a set of channels similar to or substantially the same as second set of channels 42 (shown in FIG. 2 and described above).

At an operation 608, fluid communication is established for a set of tertiary channels of the plurality of channels between the flow outlet and a second chamber of the housing, such that gas that enters the set of tertiary channels primarily flows into the second chamber. In one embodiment, operation 608 is performed by a set of channels similar to or substantially the same as third set of channels 43 (shown in FIG. 2 and described above).

At an operation 610, fluid communication is established between the first chamber and a first pressure port of the housing, such that gas flowing into the first chamber flow from the flow inlet primarily flows to the first pressure port. In one embodiment, operation 610 is performed by a pressure port similar to or substantially the same as first pressure port 31 (shown in FIG. 2 and described above).

At an operation 612, fluid communication is established between the second chamber and a second pressure port of the housing, such that gas flowing into the second chamber flow from the flow outlet primarily flows to the second pressure port. In one embodiment, operation 612 is performed by a pressure port similar to or substantially the same as second pressure port 32 (shown in FIG. 2 and described above).

At an operation 614, output signals are generated conveying information related to one or more pressure and/or flow parameters of the gas at or near the first pressure port. Furthermore, output signals are generated conveying information related to one or more pressure and/or flow parameters of the gas at or near the second pressure port. In one embodiment, operation 614 is performed by a sensor similar to or substantially the same as sensor 142 (shown in FIG. 1 and described above).

At an operation 616, a flow is determined based on the generated output signals. The flow includes one or more flow perturbations, individual ones of which correspond to individual ones of the pressure perturbations. Individual ones of the flow perturbations have a phase delay compared to the corresponding pressure perturbation that remains substantially constant across flow rates of the gas ranging between, e.g., −400 SLPM and 400 SLPM. Other ranges are also contemplated. In one embodiment, operation 616 is performed by a parameter determination module similar to or substantially the same as parameter determination module 111 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A device for measuring a differential pressure of a flow of gas between an inlet and an outlet, the device including:
   a housing that forms a conduit between an inlet and an outlet;
   a first chamber defined in the housing;
   a second chamber defined in the housing;
   a first pressure port configured to fluidly communicate with the first chamber, and
   a second pressure port configured to fluidly communicate with the second chamber; and
   a flow body disposed within the housing, the flow body comprising a plurality of channels, the plurality of channels comprising:
   a plurality of primary channels disposed within the flow body, wherein the primary channels are configured to establish fluid communication between the inlet and the outlet, such that gas from the inlet that enters the primary channels primarily flows to the outlet,
   a set of secondary channels disposed within the flow body, wherein the set of secondary channels are configured to establish fluid communication between the inlet and the first chamber, such that gas from the inlet that enters the set of secondary channels primarily flows to the first pressure port through the first chamber, and
   a set of tertiary channels disposed within the flow body, wherein the set of tertiary channels are configured to establish fluid communication between the outlet and the second chamber, such that gas that enters the set of tertiary channels primarily flows to the second pressure port through the second chamber, wherein the primary channels do not include the secondary channels or the tertiary channels, the secondary channels do not include the primary channels or the tertiary channels, and the tertiary channels do not include the primary channels or the secondary channels.

2. The device of claim 1, wherein for an individual channel from the set of secondary channels the flow body further comprises:
   an inlet-side flow director, wherein the inlet-side flow director includes an opening of the individual channel to direct flow to the first pressure port.

3. The device of claim 1, wherein for an individual channel from the set of secondary channels the flow body further comprises:
   a blocking flow director, wherein the blocking flow director includes an obstruction of the individual channel to direct flow to the first pressure port.

4. The device of claim 2, wherein the flow body has a length defined from a flow inlet of the flow body to a flow outlet of the flow body, the opening of the individual channel being disposed at or near a fraction of the length of the flow body that corresponds to a location of the first chamber when the flow body is positioned within the housing.

5. The device of claim 3, wherein the obstruction substantially prevents fluid communication between the individual channel and the second chamber.

6. The device of claim 1, wherein, responsive to gas being provided at the inlet of the housing, the provided gas including one or more pressure perturbations, individual ones of the pressure perturbations having a frequency ranging between 0 Hz and 20 Hz, the flow body is configured such that a flow based on measurements taken at the first pressure port and the second pressure port includes one or more flow perturbations, wherein individual ones of the flow perturbations correspond to individual ones of the pressure perturbations, and wherein individual ones of the flow perturbations have a phase delay compared to a corresponding pressure perturbation that remains substantially constant across flow rates of the gas ranging between minus 400 standard liter per minute (SLPM) and 400 SLPM.

7. A method for measuring a differential pressure of a flow of gas between an inlet and an outlet, the method including:
   receiving gas at a flow inlet of a flow body, wherein the flow body comprises a plurality of channels, wherein the gas includes one or more pressure perturbations, and wherein individual ones of the pressure perturbations have a frequency ranging between 0 Hz and 20 Hz;
   establishing fluid communication for primary channels of the plurality of channels between the flow inlet and a flow outlet of the flow body, such that gas from the inlet that enters the primary channels primarily flows to the outlet;
   establishing fluid communication for a set of secondary channels of the plurality of channels between the flow inlet and a first chamber of a housing arranged such that the flow body is disposed within the housing, such that gas from the flow inlet that enters the set of secondary channels primarily flows into the first chamber;
   establishing fluid communication for a set of tertiary channels of the plurality of channels between the flow outlet and a second chamber of the housing, such that gas that enters the set of tertiary channels primarily flows into the second chamber;
   establishing fluid communication between the first chamber and a first pressure port of the housing, such that gas flowing into the first chamber primarily flows to the first pressure port;
   establishing fluid communication between the second chamber and a second pressure port of the housing, such that gas flowing into the second chamber primarily flows to the second pressure port;
   generating first output signals conveying information related to one or more pressure and/or flow rate parameters of the gas at or near the first pressure port;
   generating second output signals conveying information related to one or more pressure and/or flow rate parameters of the gas at or near the second pressure port; and
   determining a flow based on the first output signals and the second output signals, wherein the flow includes one or more flow perturbations, wherein individual ones of the flow perturbations correspond to individual ones of the pressure perturbations, and wherein individual ones of the flow perturbations have a phase delay compared to a corresponding pressure perturbation that remains substantially constant across flow rates of the gas ranging between minus 400 standard liter per minute (SLPM) and 400 SLPM, wherein the primary channels do not include the secondary channels or the tertiary channels, the secondary channels do not include the primary channels or the tertiary channels, and the tertiary channels do not include the primary channels or the secondary channels.

8. The method of claim 7, wherein establishing fluid communication for the set of secondary channels between the flow inlet and the first chamber is accomplished through an inlet-side flow director, and wherein establishing fluid communication for the set of tertiary channels between the flow outlet and the second chamber is accomplished through an outlet-side flow director.

9. The method of claim 7, wherein the phase delay ranges between about minus 1 ms and 1 ms.

10. The method of claim 7, wherein the flow body has a length defined from a flow inlet of the flow body to a flow outlet of the flow body, wherein establishing fluid communication for the individual ones of the set of secondary channels between the flow inlet and the first chamber of the housing comprises:
   establishing an opening in an individual channel from the plurality of channels at or near a fraction of the length of the flow body that corresponds to a location of the first chamber when the flow body is positioned within the housing, and
   obstructing the individual channel, downstream from the opening, such that fluid communication between the individual channel and the second chamber is substantially prevented.

11. The method of claim 7, wherein the set of secondary channels and the set of tertiary channels each include more than ten individual channels from the plurality of channels.

12. A system configured to measure a differential pressure of a flow of gas between an inlet and an outlet, the system including:
   means for receiving gas at a flow body, wherein the flow body comprises a plurality of channels, wherein the gas includes one or more pressure perturbations, and wherein individual ones of the pressure perturbations have a frequency ranging between 0 Hz and 20 Hz;
   means for establishing fluid communication for a plurality of primary channels of the plurality of channels between the flow inlet and a flow outlet of the flow body, such that gas from the inlet that enters the primary channels primarily flows to the outlet;
   means for establishing fluid communication for a set of secondary channels of the plurality of channels between the flow inlet and a first chamber of a housing arranged such that the flow body is disposed within the housing, such that gas from the flow inlet that enters the set of secondary channels primarily flows into the first chamber;
   means for establishing fluid communication for a set of tertiary channels of the plurality of channels between the flow outlet and a second chamber of the housing, such that gas that enters the set of tertiary channels primarily flows into the second chamber;

means for establishing fluid communication between the first chamber and a first pressure port of the housing, such that gas flowing into the first chamber from the flow inlet primarily flows to the first pressure port;

means for establishing fluid communication between the second chamber and a second pressure port of the housing, such that gas flowing into the second chamber from the flow inlet primarily flows to the second pressure port;

means for generating first output signals conveying information related to one or more pressure and/or flow rate parameters of the gas at or near the first pressure port;

means generating second output signals conveying information related to one or more pressure and/or flow rate parameters of the gas at or near the second pressure port; and means for determining a flow based on the first output signals and the second output signals, wherein the flow includes one or more flow perturbations, wherein individual ones of the flow perturbations correspond to individual ones of the pressure perturbations, and wherein individual ones of the flow perturbations have a phase delay compared to a corresponding pressure perturbation that remains substantially constant across flow rates of the gas ranging between minus 400 standard liter per minute (SLPM) and 400 SLPM, wherein the primary channels do not include the secondary channels or the tertiary channels, the secondary channels do not include the primary channels or the tertiary channels, and the tertiary channels do not include the primary channels or the secondary channels.

13. The system of claim 12, wherein the means for establishing fluid communication for the set of secondary channels between the flow inlet and the first chamber includes an inlet-side flow director, and wherein the means for establishing fluid communication for the set of tertiary channels between the flow outlet and the second chamber includes an outlet-side flow director.

14. The system of claim 12, wherein the phase delay ranges between about minus 1 ms and 1 ms.

15. The system of claim 12, wherein the flow body has a length defined from a flow inlet of the flow body to a flow outlet of the flow body, wherein the means for establishing fluid communication for the individual ones of the set of secondary channels between the flow inlet and the first chamber of the housing comprises:

means for establishing an opening of an individual channel from the plurality of channels at or near a fraction of the length of the flow body that corresponds to a location of the first chamber when the flow body is positioned within the housing, and means for obstructing the individual channel, downstream from the opening, such that fluid communication between the individual channel and the outlet is substantially prevented.

\* \* \* \* \*